US008587410B2

(12) United States Patent
Potyrailo et al.

(10) Patent No.: US 8,587,410 B2
(45) Date of Patent: Nov. 19, 2013

(54) SYSTEM AND METHOD FOR OPERATING RFID DEVICES

(75) Inventors: Radislav Potyrailo, Niskayuna, NY (US); Vincent F. Pizzi, Westborough, MA (US); Hanno Ehring, Uppsala (SE); Cheryl M. Surman, Niskayuna, NY (US); Klaus Gebauer, Uppsala (SE); Mircea Georgescu, Uppsala (SE)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 154 days.

(21) Appl. No.: 13/145,172

(22) PCT Filed: Jan. 28, 2010

(86) PCT No.: PCT/SE2010/050083
§ 371 (c)(1),
(2), (4) Date: Jul. 19, 2011

(87) PCT Pub. No.: WO2010/087764
PCT Pub. Date: Aug. 5, 2010

(65) Prior Publication Data
US 2012/0001731 A1    Jan. 5, 2012

Related U.S. Application Data

(60) Provisional application No. 61/148,191, filed on Jan. 29, 2009.

(51) Int. Cl.
*G06K 7/01* (2006.01)
(52) U.S. Cl.
USPC .... 340/10.1; 340/572.1; 340/10.4; 340/10.41

(58) Field of Classification Search
USPC ............... 340/10.1, 10.2, 10.3, 10.31, 10.32, 340/10.33, 10.4, 10.41, 10.42, 10.5, 572.1; 711/103; 604/189, 131, 403
See application file for complete search history.

(56) References Cited

U.S. PATENT DOCUMENTS

| 7,382,255 | B2 | 6/2008 | Chung |
| 2007/0109103 | A1 | 5/2007 | Jedrey et al. |
| 2007/0249901 | A1 | 10/2007 | Ohline et al. |
| 2008/0024310 | A1 | 1/2008 | Baker et al. |
| 2008/0211638 | A1* | 9/2008 | Masui et al. ............... 340/10.51 |
| 2008/0282026 | A1 | 11/2008 | Selker et al. |
| 2009/0256679 | A1 | 10/2009 | Potyrailo et al. |
| 2009/0273447 | A1 | 11/2009 | Selker et al. |

FOREIGN PATENT DOCUMENTS

| EP | 1 887 581 | 12/2008 |
| WO | WO 2009/120231 | 10/2009 |

* cited by examiner

*Primary Examiner* — Nabil Syed

(57) ABSTRACT

This invention provides a system for operating RFID tags on a single-use connector. The system includes: a first single-use connector configured to receive a first RFID tag and a second single-use connector configured to receive a second RFID tag. The invention also includes a reader placed close to the first RFID tag and the second RFID tag. The reader is configured to: determine if the first RFID tag and the second RFID tag are gamma sterilized; determine if the first RFID tag and the second RFID tag were previously used; determine if the first RFID tag and the second RFID tag are authentic; and determine if the first RFID tag matches with the second RFID tag.

23 Claims, 10 Drawing Sheets

300

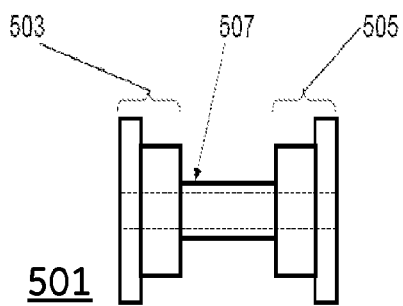
FIG. 5A
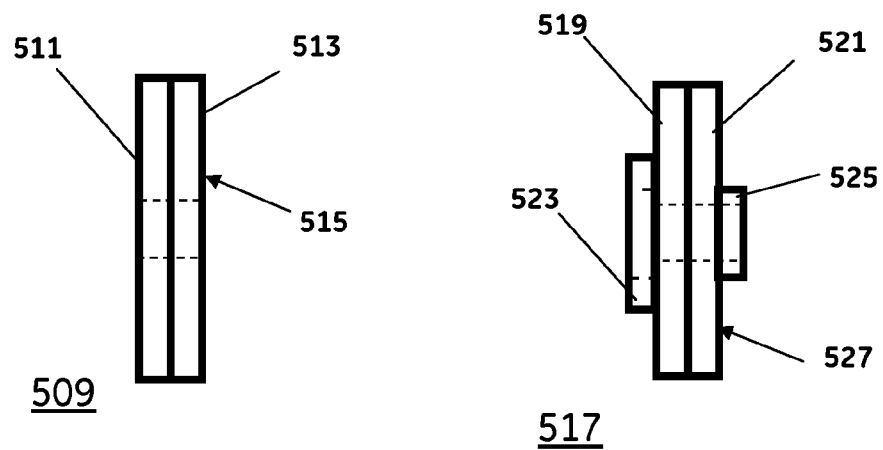
FIG. 5B
FIG. 5C

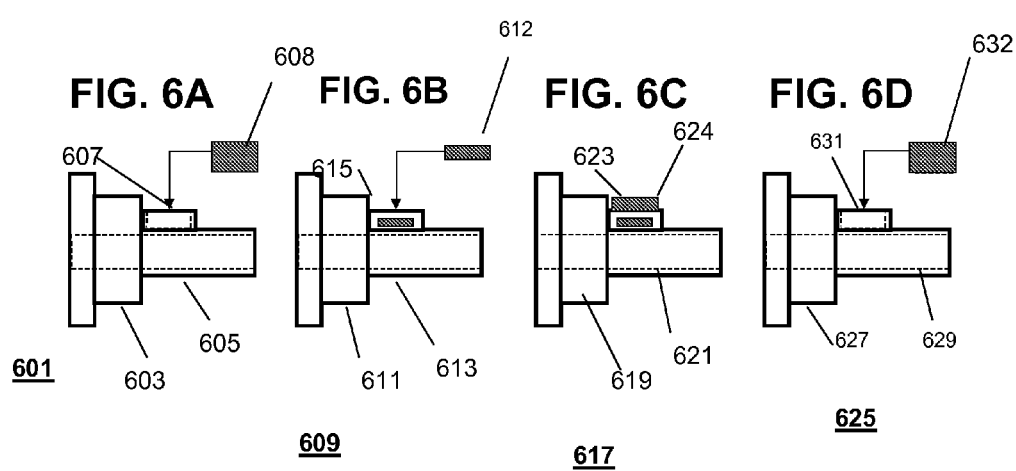

SYSTEM AND METHOD FOR OPERATING RFID DEVICES

CROSS-REFERENCE TO RELATED APPLICATIONS

This application is a filing under 35 U.S.C. §371 and claims priority to international patent application number PCT/SE2010/050083 filed Jan. 28, 2010, published on Aug. 5, 2010 as WO 2010/087764, which claims priority to U.S. provisional patent application No. 61/148,191 filed Jan. 29, 2009.

FIELD OF THE INVENTION

This invention relates to a system and method for operating radio frequency identification devices on single-use connectors.

BACKGROUND OF THE INVENTION

Radio frequency identification (RFID) tags are widely employed for automatic identification of objects, such as animals, garments etc. and detection of unauthorized opening of containers. There are several examples of RFID tags being used to identify objects.

First, there is a U.S. Pat. No. 7,195,149 for a method of attaching an RFID tag to a hose and tracking system. This hose tracking system includes a hose assembly with an attached RFID tag embedded therein during manufacture, molded thereon permanently attached. The RFID tag is coded with identification specific to the particular hose assembly. The RFID tag reader includes a user input for at least one trackable event and is at least connectable to a computer network or compatible for uploading the identification and any user input to a network accessible device. A network accessible hose database is provided, having hose-related information. The network accessible hose database provides access to a user to obtain the hose-related information based on the identification from the RFID tag that receives and stores data related to the at least one trackable event. There is also another U.S. Pat. No. 7,328,837 similar to U.S. Pat. No. 7,195,149, where U.S. Pat. No. 7,328,837 is for a method of attaching an RFID tag to a hose and tracking system.

Next, there is U.S. Pat. No. 5,892,458 that is an apparatus for the recognition of exchangeable parts in analytical measuring instruments. The apparatus for the recognition of exchangeable parts in an analytical measuring instrument or in an analytical measurement system with several analytical devices contain exchangeable parts that have identification modules that are each attached to an exchangeable part. In addition, the apparatus has transmitter receiver devices that can receive information signals from an identification module and send information signals to the identification module. The control device can cause a message to be displayed on a display device if the information read out from an identification module does not fulfill certain conditions, for example with regard to the quality.

Next, there is another U.S. Pat. No. 7,135,977 for a method and system for tracking identification devices, which includes storing data about the identification device in a register, the data to be stored including data relating to a forwarding location that requests information about the identification device should be forwarded. The identification device is attached to an item to be monitored. The method includes accessing the register when the identification device has been read and a request for information has been received. Details of the forwarding location are obtained from the register. The request is forwarded to the forwarding location and the requested information about the identification device is sent from the forwarding location to a requester of the information.

While the aforementioned RFID inventions have been able to identify devices associated with the RFID tags, these inventions are not able to accurately determine if one RFID tag is matched to one or more RFID tags in order for these RFID tags to operate with each other, which is necessary to prevent utilization of corrupt RFID tags. Therefore, there is a need for an apparatus and system that is able to determine if one RFID tag can be authentically matched with another RFID tag to prevent illegal manufacturing of disposable bioprocess components, especially those that are sterilized by gamma irradiation or other suitable means of lowering bioburden of the disposable or limited reuse device.

BRIEF SUMMARY OF THE INVENTION

The present invention has been accomplished in view of the above-mentioned technical background, and it is an object of the present invention to provide a system and method for operating RFID tags on single-use connectors.

In a preferred embodiment of the invention, there is a system for operating RFID tags on a single-use connector. The system includes: a first single-use connector configured to receive a first RFID tag and a second single-use connector configured to receive a second RFID tag. The invention also includes a reader placed close to the first RFID tag and the second RFID tag. The reader is configured to: determine if the first RFID tag and the second RFID tag are gamma sterilized; determine if the first RFID tag and the second RFID tag were previously used; determine if the first RFID tag and the second RFID tag are authentic; and determine if the first RFID tag matches with the second RFID tag.

In another preferred embodiment of the invention, there is an apparatus for operating RFID tags. The apparatus includes a reader placed close to a first RFID tag with a first single-use connector and a second RFID tag with a second single-use connector. The reader is configured to: determine if the first RFID tag and the second RFID tag are gamma sterilized; determine if the first RFID tag and the second RFID tag were previously used; determine if the first RFID tag and the second RFID tag are authentic; and determine if the first RFID tag matches with the second RFID tag.

BRIEF DESCRIPTION OF THE DRAWINGS

These and other advantages of the present invention will become more apparent as the following description is read in conjunction with the accompanying drawings, wherein:

FIGS. 5A-C show a single-use connector design with two opposite flanges in accordance with an embodiment of the invention;

FIG. 6A-D shows several single-use connector designs that incorporate RFID tags in accordance with an embodiment of the invention;

DETAILED DESCRIPTION OF THE INVENTION

The presently preferred embodiments of the invention are described with reference to the drawings, where like components are identified with the same numerals. The descriptions of the preferred embodiments are exemplary and are not intended to limit the scope of the invention.

Figure 1:
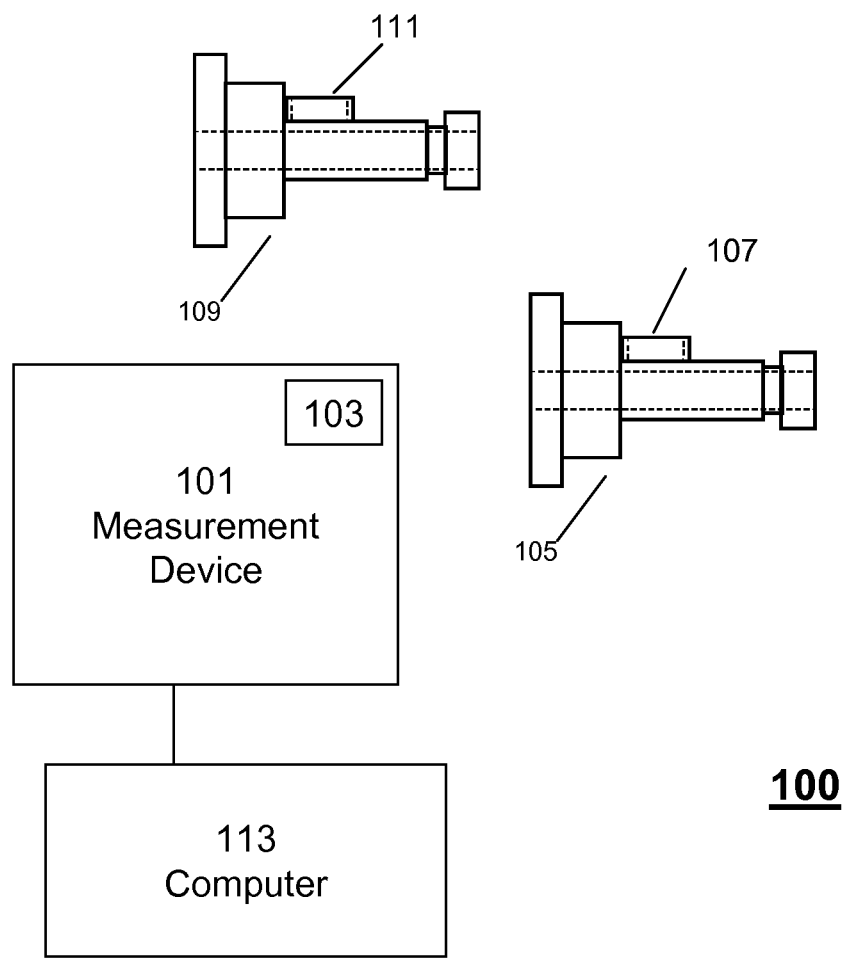
FIG. 1 illustrates a block diagram of a system in accordance with an embodiment of the invention.

FIG. 1 illustrates a block diagram of a system for determining if radio frequency identification (RFID) tags are operating normally on single-use connectors. The system 100 includes a typical measurement device (writer/reader) 101 that includes a reader 103, a first single-use connector 105 with a first RFID tag 107, a second single-use connector 109 with a second RFID tag 111 and a computer 113. This computer 113 is connected to the measurement device 101. Reader 103 receives and sends information back and forth to the computer 113. Also, this information can be sent wirelessly or by wire when using a cable. Computer 113 includes typical components associated with a computer, such as a memory that includes a database. This database includes information related to RFID tags 107 and 111 and any other typical tags. This information includes: the gamma-sterilization of relevant RFID tags, such as RFID tags 107 and 111, the usage (including pass, current and future utilization of RFID tags) of RFID tags, such as RFID tags 107 and 111, if RFID tags 107 and 111 are authentic RFID tags, if relevant RFID tags, such as RFID tags 107 and 111 can be matched with each other and if RFID tags 107 and 111 should be operable with each other. A user may install all of the aforementioned information into the database of the computer 113. In another preferred embodiment of the invention, even though only two RFID tags are used in this invention 3, 4, 20, 100 or more RFID tags may be used in the place of the RFID tags on the single-use connectors. Single-use connectors 105 and 109 may also be referred to as single-use bioprocess components. Other examples of single-use bioprocess components include storage bags, bioreactors, filters, tubing, and separation columns.

First RFID tag 107 is incorporated into the first single-use connector 105 by any of the methods disclosed below in FIGS. 6A-6D. Second RFID tag 111 is incorporated into the second single-use connector 109 by any of the methods disclosed below in FIGS. 6A-6D. Reader/writer 103 is a typical reader/writer device from Wave Logic LLC (Scotts Valley, Calif.), from SkyeTek (Westminster, Col.), or from other sources. RFID tags 107 and 111 (on-board rectification bridge and other RF front-end devices) include a non-volatile memory. The tags 107 and 111 are energized by a time-varying electromagnetic radio frequency (RF) wave (called a carrier signal) that is transmitted by the reader 103. RFID tags may be operating at a frequency in the range of over 120-140 kHz, around 13.56 MHz, over 800-980 MHz around 2.45 GHz and 5.8 GHz. Also, the RFID tags 107 and 111 can include: integrated circuits memory chips, read-write memory, read-only memory and no memory (chip-less tags). In operation of RFID tags 107 and 111, the frequency range of 120-140 kHz is known as low frequency (LF), the frequency range around 13.56 MHz is known as high frequency (HF), the frequency range of 800-980 MHz is known as ultra-high frequency (UHF), the frequency range around 2.45 GHz and 5.8 GHz is known as microwave frequency (MF).

Reader 103 is a microcontroller-based unit with an output coil, peak detector hardware, comparators, and firmware designed to transmit energy to a tag (RFID tags 107 and 111) and read information back from it by detecting the backscatter modulation. When the RF field passes through an antenna coil, an AC voltage is generated across the coil. This voltage is rectified by the modulation circuitry of the memory chip to supply power to the RFID tags 107 and 111. The information stored in the RFID tags 107 and 111 are transmitted back (backscattered) to the reader 103. The reader 103 demodulates the signals received from the tag antenna of the tags 107 and 111, and decodes the signal for further processing.

Figure 2:
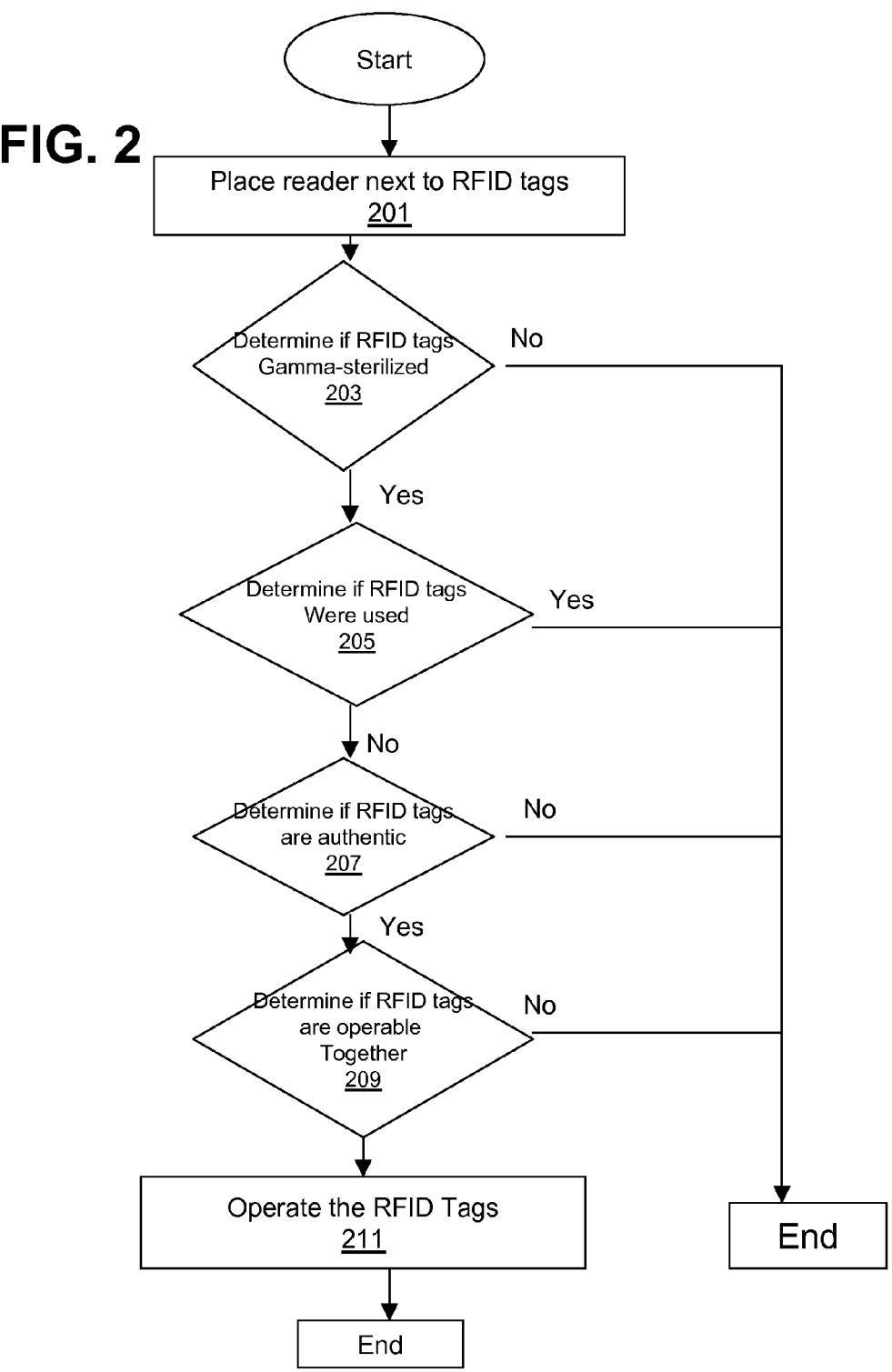
FIG. 2 is a flow-chart of how RFID tags of FIG. 1 are utilized in accordance with an embodiment of the invention.

FIG. 2 shows a flow-chart of how the reader determines if the RFID tags are operable. At block 201, the reader 103 is placed next to the first single-use connector 105 with a first RFID tag 107 and the second single-use connector 109 with the second RFID tag 111 as shown in FIG. 1. There is a read range the reader 103 needs to be from the first RFID tag 107 and the second RFID tag 111. This read range depends on several factors, including the operating frequency, power of the reader, geometry of the RFID tag, geometry of the reader antenna, angular position of the reader in the relation to the tag, amount of clutter between the tag and the reader, and other parameters. The read range can be from less than several millimeters to several meters. For example, the distance between the reader 103 and the first RFID tag 107 and the second RFID tag 111 may be anywhere from 1-100 millimeters to 1-20 meters.

Next, at block 203 the reader 103 determines if the RFID tag 107 and the RFID tag 111 is gamma-sterilized. As stated above, the reader 103 is able to access information on the computer 113 about the RFID tags 107 and 111. When the reader 103 receives this information, the reader 103 checks to see if the RFID tags 107 and 111 are gamma-sterilized. If the RFID tags are not gamma-sterilized then this process ends. However, if the RFID tags 107 and 111 are gamma sterilized then this process continues to block 205. Also, the gamma sterilization of the RFID tags 107 and 111 leads to the alteration of the read range and the powering requirements of the IC memory chip of the tag. These alterations can be also used to determine if the tags has been irradiated. For example the read range between the reader 103 and RFID tags 107 and 111 is changed from 5-70 millimeters (before the gamma irradiation) to 15-55 millimeters (after gamma irradiation) of RFID tags 107 and 111.

At block 205, the reader 103 accesses the information about the RFID tags 107 and 111 stored on the computer 113 to determine if the RFID tags 107 and 111 were previously used. If the reader 103 finds out that the RFID tags 107 and 111 have been used then this process ends. However, if the reader 103 determines that the RFID tags 107 and 111 were not previously used then this process continues to block 207.

Next at block 207, the reader 103 accesses the information stored about the RFID tags 107 and 111 on the computer to determine if the RFID tags 107 and 111 are authentic. Reader 103 accesses information on the computer 113 about RFID tags 107 and 111. If the reader 103 checks that the RFID tags 107 and 111 are not authentic then this process ends. However, if the reader 103 determines that the RFID tags 107 and 111 are authentic then this process continues to block 209.

At block 209, the reader 103 accesses the information stored about the RFID tags 107 and 111 on the computer 113 to determine if the RFID tags 107 and 111 match each other and are operable with each other. RFID tags 107 and 111 are matchable when they are positioned into or onto connectors 105 and 109 where the connectors are intended to be connected together. If connectors 105 and 109 are not intended to be connected together as per the design of the manufacturing system, this information will be in the database of the computer 113. When these connectors happen to be mistakenly or otherwise incorrectly connected, their associated RFID tags 107 and 111 are scanned with the reader 103 and the reader (or computer or another device) sends a message to the computer 113 s that the connection is not correct. Reader 103 accesses information on the computer 113 about RFID tags 107 and 111. If the reader 103 checks that the RFID tags 107 and 111 are not operable with each other then this process ends. However, if the reader 103 determines that the RFID tags 107 and 111 are operable with each other then the RFID tags 107 and 111 are fully operable with each other at block 211. For two or more RFID tags to operate with a single RFID reader, known anti-collision algorithms are applied. Tag collision in RFID systems happens when the RFID tag reader 103 energizes multiple tags simultaneously, and reflects their respective signals back to the reader at the same time. This problem is typical when a large number of tags must be read together in the same RF field. The reader is unable to differentiate these signals; tag collision confuses the reader 103. Several known anti-collision algorithms are stored on the computer 113 and accessed and utilized by the measurement device 101 and the reader 103 to keep radio frequency waves from one tag from interfering with radio frequency waves from another tag. Examples of anti-collision algorithms, which may be utilized in this invention, include bit-based algorithm, binary tree algorithm, Dynamic Slot Allocation (DSA) algorithm, and ALOHA-based algorithms (such as ALOHA, slotted ALOHA, frame slotted ALOHA and dynamic frame slotted ALOHA). After the RFID tags 107 and 111 operate with each other then this process ends. While FIG. 2 shows sequential operation of steps 203, 205, 207, and 209, in another embodiment, these steps can be performed in another order or these steps can be performed in parallel.

Figure 3:
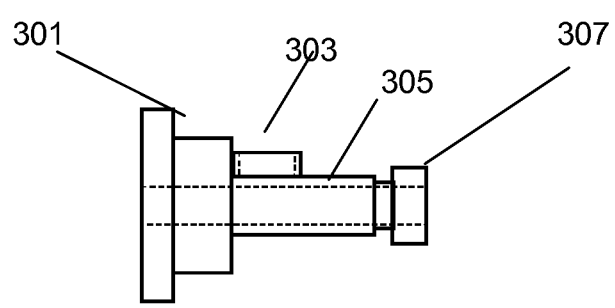
FIG. 3 shows an example of a typical single-use connector in accordance with an embodiment of the invention.

FIG. 3 shows a typical single-use connector. Single-use connector 300 includes: a flange 301, a venting port 303, an extender 305 and a flow connector cap 307. The single-use connector 300 has different types and sizes of extenders 305 and sometimes includes venting ports 303. Also, the single-use connector 300 may have typical RFID tags located in flanges, extenders, and any other locations on the connector 300. Preferred geometries of the RFID tags are round or circular, but other geometries can be used for similar purposes.

The initial observations of gamma radiation resistance of ferroelectric memory (FRAM) go back to several decades ago. Scott, J. F.; Paz De Araujo, C. A., "Ferroelectric memories", *Science* 1989, 246, 1400-1405 and Benedetto, J. M.; DeLancey, W. M.; Oldham, T. R.; McGarrity, J. M; Tipton, C. W; Brassington, M.; Fisch, D. E., "Radiation evaluation of commercial ferroelectric nonvolatile memories", *IEEE Trans. Nucl. Sci.* 1991, 38 (6 pt 1), 1410-1414. Now, FRAM is the most widely explored type of a radiation tolerant non-charge-based storage memory. Scott, J. F.; Paz De Araujo, C. A., "Ferroelectric memories", *Science* 1989, 246, 1400-1405; Messenger, G. C.; Coppage, F. N., "Ferroelectric memories: A possible answer to the hardened nonvolatile question", *IEEE Trans. Nucl. Sci.* 1988, 35 (6 pt 1), 1461-1466; and Scott, J. F.; Araujo, C. A.; Meadows, H. B.; McMillan, L. D.; Shawabkeh, A., "Radiation effects on ferroelectric thin-film memories: Retention failure mechanisms" *J. Appl. Phys.* 1989, 66, 1444-1453.

An RFID memory chip that can be gamma radiation resistant includes FRAM memory material and a complementary metal-oxide-semiconductor (CMOS) circuitry. In order to achieve ability to use the memory chip device of an RFID tag for operation with gamma-sterilized components, it is critical to address: (1) material limitations of the non-charge-based non-volatile storage memory material and (2) device limitations of the CMOS circuitry of the IC memory chip as a whole device upon exposure to gamma radiation.

On the material level, while the ferroelectric material is more gamma radiation resistant than EEPROM, it still experiences gamma-irradiation effects from the common $^{60}$Co and $^{137}$Cs gamma radiation sources that emit gamma rays of 1.17 and 1.33 MeV ($^{60}$Co) and 0.6614 MeV ($^{137}$Cs). Scott, J. F.; Paz De Araujo, C. A., "Ferroelectric memories", *Science* 1989, 246, 1400-1405; Derbenwick, G. F.; Isaacson, A. F., "Ferroelectric memory: on the brink of breaking through", *IEEE Circuits & Devices* 2001, Jan. 20-30; and Scott, J. F.; Araujo, C. A.; Meadows, H. B.; McMillan, L. D.; Shawabkeh, A., "Radiation effects on ferroelectric thin-film memories: Retention failure mechanisms" *J. Appl. Phys.* 1989, 66, 1444-1453.

This energy of gamma radiation is high enough to potentially cause the displacement damage in the ferroelectric material. Schwank, J. R.; Nasby, R. D.; Miller, S. L.; Rodgers, M. S.; Dressendorfer, P. V., "Total-dose radiation-induced degradation of thin film ferroelectric capacitors", *IEEE Trans. Nucl. Sci.* 1990, 37 (6 pt 1), 1703-1712.

Indeed, after an exposure to a gamma radiation, ferroelectric material experiences the decrease in retained polarization charge due to an alteration of the switching characteristics of the ferroelectric due to changes in the internal fields. This radiation-induced degradation of the switching characteristics of the ferroelectric is due to transport and trapping near the electrodes of radiation-induced charge in the ferroelectric material. Once trapped, the charge can alter the local field around the dipoles, altering the switching characteristics as a function of applied voltage. Two known scenarios for trap sites are at grain boundaries or in distributed defects in the ferroelectric material, depending on the fabrication method of FRAM (for example, sputtering, sol-gel deposition, spin-on deposition, metal-organic chemical vapor deposition, liquid source misted chemical deposition). In addition to the charge trapping, gamma radiation can also directly alter the polarizability of individual dipoles or domains.

On the device level, the FRAM memory chip of the RFID tag consists of a standard electric CMOS circuitry and an array of ferroelectric capacitors in which the polarization dipoles are oriented during the memory write operation of the FRAM. In these capacitors, a ferroelectric material is used as a dielectric film of a capacitor to store data. The FRAM device has two modes of memory degradation that include functional failure and stored data upset. Thus, the radiation response effects in the memory chip are a combination of non-volatile memory and the CMOS components in the memory chip. Radiation damage in CMOS includes but is not limited to the threshold voltage shift, increased leakage currents, and short-circuit latchup.

In conventional CMOS/FRAM memory devices, the gamma radiation induced loss of device performance (the ability to write and read data from the memory chip) is dominated by the unhardened commercial CMOS components of the memory chip. Benedetto, J. M.; DeLancey, W. M.; Oldham, T. R.; McGarrity, J. M.; Tipton, C. W.; Brassington, M.; Fisch, D. E., "Radiation evaluation of commercial ferroelectric nonvolatile memories", *IEEE Trans. Nucl. Sci.* 1991, 38 (6 pt 1), 1410-1414; and Coiec, Y. M.; Musseau, O.; Leray, J. L., A study of radiation vulnerability of ferroelectric material and devices, *IEEE Trans. Nucl. Sci.* 1994, 41, 495-502.

Hardened-by-design techniques can be used to manufacture radiation-hardened CMOS components of semiconductor memory. The examples of hardened-by-design CMOS components include p-channel transistors in memory array, annular n-channel gate structures, p-type guard rings, robust/redundant logic gates protecting latches, and latches immune to single event effects. Kamp, D. A.; DeVilbiss, A. D.; Philpy, S. C.; Derbenwick, G. F., "Adaptable ferroelectric memories for space applications", *Non-Volatile Memory Technology Symposium, NVMTS04* 2004, 149-152; and Kamp, D. A.; DeVilbiss, A. D.; Haag, G. R.; Russell, K. E.; Derbenwick, G. F., "High density radiation hardened FeRAMs on a 130 nm CMOS/FRAM process', *Non-Volatile Memory Technology Symposium, NVMTS05* 2005, 48-50.

The hardened-by-design techniques prevent radiation-hard latches from being set by single event transients (SET) propagating through the logic of the device. Applications of FRAM memory in RFID tags were described earlier in U.S. Pat. Nos. 6,808,952 and 6,201,731.

Applications of FRAM memory in RFID tags upon a gamma radiation exposure were also described in U.S. Pat. No. 6,806,808.

Our detailed understanding of the ferroelectric material and CMOS device aspects of performance of FRAM-based RFID tags has been further coupled with our experiments with available and our custom-fabricated tags. We have observed that there is a significant failure rate of gamma-irradiated RFID tags where the data from the irradiated tag cannot be read and no new data can be written to the irradiated tag. Prior work on FRAM-based memory chips suggested that the gamma radiation induced loss of device performance originates from two independent sources such (1) radiation effects on the non-charge-based storage memory material and (2) radiation effects on the performance of analog and digital CMOS circuit components of an IC memory chip.

Thus, in order to significantly improve the reliability of performance of FRAM-based RFID tags, we have critically analyzed the remaining challenges and introduced gamma-sterilizable RFID tag technology to provide reliable identification, tracking, and authentication of sterilized bioprocess components. We have found that to boost the performance reliability of gamma-resistant RFID tags, two approaches should be utilized.

The first approach is the implementation of a temporary redundancy of written data that is critical to successfully pass the gamma irradiation step. After the gamma irradiation, the data redundancy can be released to free up the memory for the user-defined data on the FRAM memory chip. This approach targets primarily the possible failures of ferroelectric capacitors in the memory of the IC chip.

The second approach is to interrogate the RFID tag with a variable RF power to present the tag with several allowed power levels. Due to the gamma radiation exposure, the CMOS components of the IC chip change their electrical characteristics. As a result, the read/write power levels employed before the gamma irradiation of the tag become modified after the gamma irradiation. This approach targets primarily the possible failures of CMOS circuitry of the IC chip.

These two approaches provide the capability of not only to dramatically improve the reliability of the tag performance but also to provide a signature of a gamma-irradiated tag. Such signature can be related to the gamma exposure dose of the tag, so the RFID tag will serve as an indicator of gamma sterilization or as a reliable dosimeter.

Figures 4A, 4B:
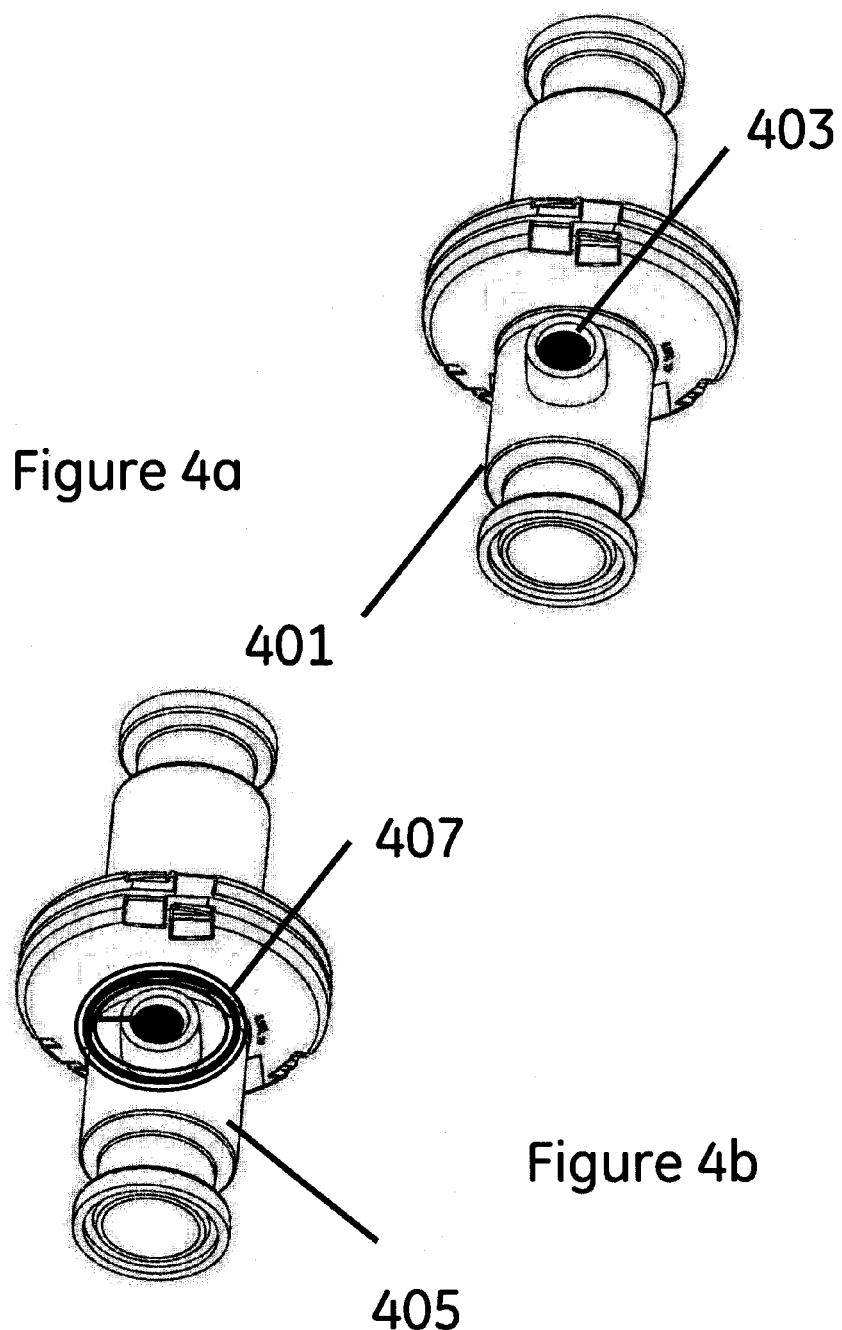
FIGS. 4A and 4B illustrate a schematic of RFID tags incorporated into round geometries of single-use connectors and into circular geometries of the single-use connectors in accordance with an embodiment of the invention.

FIGS. 4A and 4B illustrate RFID tags incorporated into single-use connectors. Single-use connector 401 includes a round RFID tag 403. Single-use connector 405 includes a circular RFID tag 407. RFID tags 403 and 407 are equivalent to RFID tags 107 and 111 described above. Even though the RFID tags 403 and 407 have a round or circular geometry these RFID tags may have any shape. RFID tags 403 and 407 are gamma radiation resistant to typical levels required for pharmaceutical processing (25 to 50 kGy). The gamma radiation resistance (immunity to effects of gamma radiation) is provided in several ways: 1. from the storage of required digital information that allows its error correction; 2. from the use of radiation-hardened CMOS circuitry on RFID tag or from control of recovery of the standard CMOS after gamma irradiation; 3. from the use of FRAM memory; and 4. from the reading of the RFID tag after gamma radiation with different power levels of the reader or at different distances between the reader and the RFID tag.

FIG. 5A is a typical single-use connector design with two opposite flanges. Single-use connector 501 has two opposite flanges 503 and 505 with an extender 507 in between the flanges. A RFID tag would be incorporated or located in the extender 507 in between the flanges 503 and 505.

FIG. 5B is a typical single-use connector design with two opposite flanges of a genderless type. Single-use connector 509 has two opposite flanges of a genderless type 511 and 513. A RFID tag 515 would be incorporated or located within the flanges 511 and 513.

FIG. 5C is a typical single-use connector design with two opposite flanges of a male/female type. Single-use connector 517 has two opposite flanges 519 and 521. A female adapter 523 is located on the outer face of flange 519, and a male adapter 525 is located on the outer face of flange 521. A RFID tag 527 would be incorporated or located within the flanges 519 and 521.

FIGS. 6A, 6B, 6C and 6D show several single-use connectors that incorporate RFID tags in various ways. For FIG. 6A, single-use connector 601 includes a flange 603 with an extender 605. On top of the extender 605 there is a RFID insertion point 607 where a RFID tag 608 will be located. In FIG. 6B, single-use connector 609 includes the flange 611 and the extender 613. A RFID sensor 612 is molded (or permanently attached) into an insertion point 615 of the extender 613 for comfortable placement of the RFID sensor 612 in the extender 613.

In FIG. 6C, single-use connector 617 includes the flange 619 and the extender 621. A RFID sensor 624 and a pick up are molded into an insertion point 623 of the single-use connector 617. For FIG. 6D, single-use connector 625 includes a flange 627 and the extender 629. This time a factor will insert the RFID sensor 632 assembly into the pre-molded location or insertion point 631 of the extender 629.

Figure 7:
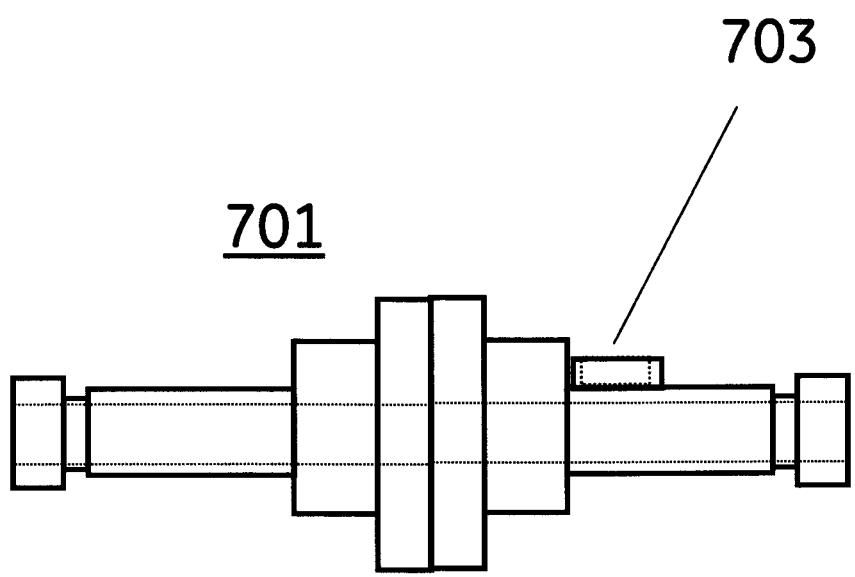
FIG. 7 shows an RFID tag integrated into a single-use connector in accordance with the invention.

FIG. 7 shows an RFID tag integrated into a single-use connector. This single-use connector is a typical single-use connector 701 that has a pre-molded location where a RFID tag 703 is located. RFID tags for this invention are fabricated with FRAM memory chips MB89R118A (Fujitsu Corp., Japan). These chips are made using a standard 0.35-μm CMOS circuitry coupled with the ferroelectric memory. The total memory of the MB89R118A chips is 2000 bytes. The FRAM memory chips were integrated into RFID tags with a 10-mm diameter antenna geometry. Writing and reading of digital data was performed using a Reader/Writer from Wave Logic LLC (Scotts Valley, Calif.). The digital ID was measured from the integrated RFID tag as E008 011 1ACO D948.

Figure 8:
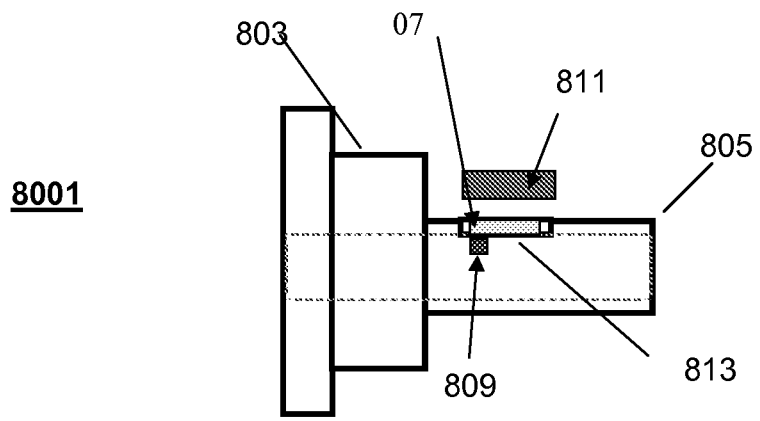
FIG. 8 shows the integration of an RFID tag into a single-use connector in accordance with an embodiment of the invention

FIG. 8 shows an integration of RFID pressure sensor into a single-use connector. Single-use connector 801 includes a flange 803 and an extender 805. Extender 805 includes a pre-molded location where a RFID tag 807, a pressure sensor 809 and a pick up coil 811 are placed. Pick up coil 811 is attached via a registration point located on the extender 805 that provides a set distance between the pick up coil 811 and the RFID tag 807 with the pressure sensor 809. This attachment can be performed by a plurality of methods: manually registering or automating placement of the pick up coil 811 to the predetermined point of contact with the extender 805, followed by sonic or thermal welding or solvent bonding or physical capture to achieve an integral seal with the pick up coil 811 and the extender 805. A pressure RFID sensor 813 is fabricated by connecting the pre-fabricated RFID tag 807 with a pressure sensor 809. The resulting sensor has a resonant structure. RFID pressure sensor 813 is integrated into the connector 801 using a method of a pre-molded location. Some examples of other RFID sensors in single-use connectors and components include temperature sensors, pH sensors, conductivity sensors, dissolved oxygen sensors, carbon dioxide sensors, and glucose sensors.

Figure 9:
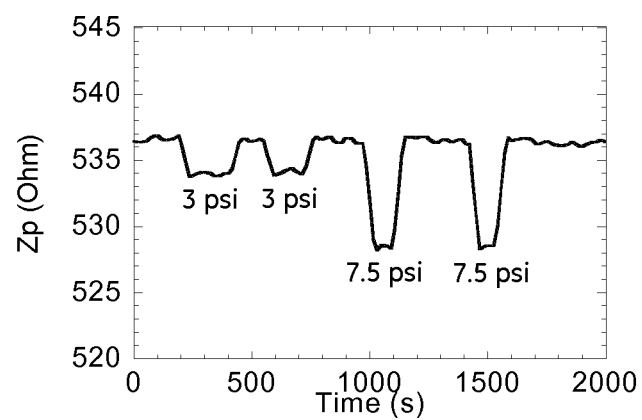
FIG. 9 is a graphical representation of a pressure response of the RFID tag integrated into a single-use connector in accordance with the invention.

FIG. 9 is a graphical representation of a pressure response of the RFID tag integrated into a single-use connector. Measurements of the complex impedance of the RFID sensor were performed using a network analyzer under a computer control using LabVIEW. The analyzer was used to scan the frequencies over the range of interest (typically centered at 13 MHz with a scan range of ~10 MHz) and to collect the complex impedance response from the RFID sensor. The collected complex impedance data was analyzed using Excel (Microsoft Inc. Seattle, Wash.) or KaleidaGraph (Synergy Software, Reading, Pa.) and PLS_Toolbox (Eigenvector Research, Inc., Manson, Wash.) operated with Matlab (The Mathworks Inc., Natick, Mass.). Writing and reading of digital data was performed using a Reader/Writer from Wave Logic LLC (Scotts Valley, Calif.). The digital ID was measured from the integrated RFID pressure sensor as E008 011 1ACO D9CA. In operation of the pressure RFID sensor, the initial reading of the sensor was ~536 Ohm. Upon an application of pressure (for example, 3 psi, and 7.5 psi), the sensor signal changed to ~534 and ~528 Ohm, respectively.

Figure 10:
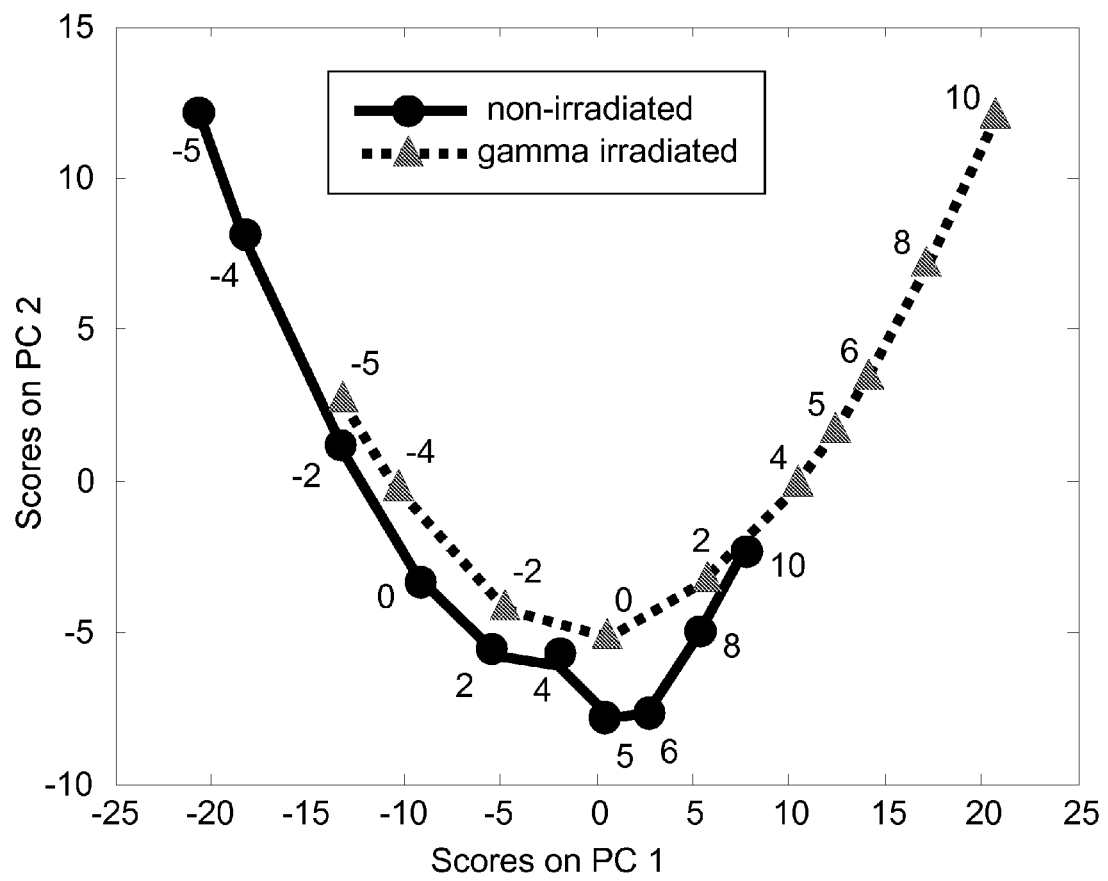
FIG. 10 is result of a graphical illustration of a result of principal components analysis of frequency response of a RFID tag before and after gamma irradiation.

FIG. 10 is a graphical representation of differences in operational characteristics of HF RFID tags with FRAM-based memory chips MB89R118A (Fujitsu Corp., Japan) before and after gamma irradiation at 35 kGy. It is well known that to operate (to activate) the memory chip, it is important to apply the correct amount of RF energy to the tag. The activation of the memory chip is pronounced in the changes in the frequency response of the RFID tag upon the tag excitation with a network analyzer. Measurements of activation of the RFID tags were performed at different power levels of the network analyzer ranging from −5 dBm to +10 dBm. Such measurements were performed with RFID tags before and after their gamma irradiation. The measured frequency response spectra were further processed using principal components analysis (PCA) method in order to quantitatively compare the complex shapes of the frequency spectra. FIG. 10 illustrates results of spectral analysis using PCA method. In this plot, each original spectrum is represented as a single data point and is labeled with a number, which is a power level (in dBm) from the network analyzer. The closer such data points are on this PCA plot, the more similar are the original spectra. This PCA plot shows that as expected, frequency spectra change as a function of applied power from the network analyzer because of the activation of the FRAM memory chip on the RID tag. Also, as known from literature about effects of gamma radiation on CMOS and FRAM components of FRAM memory chips, the power-activation conditions of the memory chip are changed after its gamma irradiation. This change is conclusively shown as the differences in frequency responses of FRAM memory chips before and after their gamma irradiation.

This invention provides a system and apparatus that is able to authenticate and determine if at least two RFID tags will be operable with each other. A user is able to determine if at least one RFID tag on a single-use connector is operable with another RFID tag on a single-use connector by: determining out if a first RFID tag and the second RFID tag are gamma sterilized, determining if the first RFID tag and the second RFID tag were previously used, determining if the first RFID tag and the second RFID tag are authentic, and determining if the first RFID tag matches with the second RFID tag. This invention includes a method for authenticating the RFID tags that reduces liability in that a counterfeit poor quality single-use connectors are not used in the bioprocess and/or a counterfeit poor quality RFID tags are not used on the single-use connectors.

It is intended that the foregoing detailed description of the invention be regarded as illustrative rather than limiting and that it be understood that it is the following claims, including all equivalents, which are intended to define the scope of the invention.

What is claimed is:

1. A system comprising:
a reader configured to be positioned within a read range of a first radio frequency identification (RFID) tag coupled to a first connector and a second RFID tag coupled to a second connector, wherein the reader is configured to interrogate the first and second RFID tags with a variable radio frequency (RF) energy or at different distances within the read range and determine if the first RFID tag and the second RFID tag have been gamma sterilized based on signals received from the first and second RFID tags, wherein the reader determines that the first connector and/or the second connector are gamma sterilized if the reader determines that a signature received from the respective RFID tag has been changed by gamma radiation, and wherein the reader is also, based on the signals received from the first and second RFID tags, configured to at least one of:
determine whether the first and second connectors were previously used;
determine whether the first and second connectors are authentic; or
determine whether the first RFID tag matches with the second RFID tag.

2. The system of claim 1, wherein the reader determines that the first connector and/or the second connector have been gamma sterilized by analyzing the signals to determine if operational characteristics of the respective RFID tag have been altered.

3. The system of claim 1, wherein the first RFID tag is operable with the second RFID tag if: the first RFID tag and the second RFID tag are gamma sterilized; the first connector and the second connector were not previously used; the first connector and the second connector are authentic; and the first RFID tag matches with the second RFID tag.

4. The system of claim 1, further comprising a computer that is operably connected to the reader, the computer including a memory having a database, the database having information that is related to the first and second RFID tags.

5. The system of claim 1, wherein the reader is configured to read signals having a high frequency (HF).

6. The system of claim 1, wherein the reader is configured to read signals having a microwave frequency (MF).

7. The system of claim 1, wherein the reader is configured to read signals having an ultra-high frequency (UHF).

8. The system of claim 1, wherein the read range is between 0.5 millimeters and 20 meters.

9. A system comprising:
a reader configured to be positioned within a read range of a first RFID tag coupled to a first bioprocess component and a second RFID tag coupled to a second bioprocess component, wherein the reader is configured to interrogate the first and second RFID tags and determine whether the first RFID tag and the second RFID tag have been gamma sterilized based on detected changes in operational characteristics of the respective RFID tags, wherein the reader determines that the first bioprocess component and/or the second bioprocess component are gamma sterilized if the reader determines that a signature received from the respective RFID tag has been changed by gamma radiation, and wherein the reader is also, based on signals received from the first and second RFID tags, configured to at least one of:
determine whether the first and second connectors were previously used;
determine whether the first and second connectors are authentic; or
determine whether the first RFID tag matches with the second RFID tag.

10. A system comprising:
a first bioprocess component having a first RFID tag;
a second bioprocess component having a second RFID tag; and
a reader configured to be positioned within a read range of the first RFID tag and the second RFID tag, wherein the reader is configured to interrogate the first and second RFID tags and determine whether the first RFID tag and the second RFID tag have been gamma sterilized, the gamma sterilization leading to detectable corruption of the RFID tag, the reader being configured to determine that the first bioprocess component and/or the second bioprocess component are gamma sterilized if the reader determines that a signature received from the respective RFID to has been changed by gamma radiation, and wherein the reader is also, based on signals received from the first and second RFID tags, configured to at least one of:
determine whether the first and second connectors were previously used;
determine whether the first and second connectors are authentic; or
determine whether the first RFID tag matches with the second RFID tag.

11. The system of claim 10, wherein the detectable corruption of the first RFID tag upon the gamma sterilization does not render the first and second RFID tags unreadable.

12. The system of claim 11, wherein at least one of the first and second RFID tags include a radiation hardened CMOS circuit.

13. The system of claim 11, wherein at least one of the first and second RFID tags include FRAM memory.

14. The system of claim 12, wherein the reader uses algorithms to correct for radiation effects on operational parameters of the CMOS circuit.

15. The system of claim 13, wherein the reader uses algorithms to correct for radiation effects on operational parameters of the FRAM memory.

16. The system of claim 10, wherein the first RFID tag operates also as an RFID sensor.

17. The system of claim 10, wherein the first RFID tag has at least one sensor input.

18. The system of claim 10, wherein the first RFID tag operates also as an RFID sensor for sensing at least one of pressure, temperature, pH, conductivity, dissolved oxygen, carbon dioxide, or glucose.

19. The system of claim 9, further comprising a computer operably connected to the reader, the computer having a memory with a database, the database including information relating to the first and second RFID tags.

20. The system of claim 9, wherein the reader is configured to interrogate the first and second RFID tags with a variable radio frequency (RF) energy or at different distances within the read range to receive the respective signatures.

21. The system of claim 10, further comprising a computer operably connected to the reader, the computer having a memory with a database, the database including information relating to the first and second RFID tags.

22. The system of claim 1, wherein the reader is configured to read the respective signatures simultaneously.

23. The system of claim 9, wherein the reader is configured to read the respective signatures simultaneously.

* * * * *